United States Patent [19]

Chang et al.

[11] Patent Number: 5,730,153
[45] Date of Patent: Mar. 24, 1998

[54] SURGICAL APPARATUS

[75] Inventors: Stanley Chang, 79 Greenacres Ave., Scarsdale, N.Y. 10583-1107; Nancy Cimitile, New York, N.Y.; Clarice Jaget, New York, N.Y.; Liebert Turner, New York, N.Y.

[73] Assignee: Stanley Chang, Scarsdale, N.Y.

[21] Appl. No.: 283,859

[22] Filed: Aug. 1, 1994

[51] Int. Cl.⁶ ........................... A61F 5/37
[52] U.S. Cl. ............... 128/846; 128/847; 128/857
[58] Field of Search ................... 128/846, 845, 128/842, 847–856; 600/21, 22

[56] References Cited

U.S. PATENT DOCUMENTS

| | | | |
|---|---|---|---|
| 4,275,719 | 6/1981 | Mayer | 128/849 |
| 4,476,860 | 10/1984 | Collins | 128/852 |
| 4,739,753 | 4/1988 | Brehm | 128/849 |
| 5,010,899 | 4/1991 | Thompson | 128/849 |
| 5,020,546 | 6/1991 | Russo | 128/849 |
| 5,074,316 | 12/1991 | Dowdy | 128/849 |
| 5,078,154 | 1/1992 | Patal | 128/849 |
| 5,080,108 | 1/1992 | Roth | 128/849 |
| 5,140,997 | 8/1992 | Glassman | 128/849 |
| 5,178,162 | 1/1993 | Bose | 128/849 |
| 5,316,541 | 5/1994 | Fischer | 128/853 |

Primary Examiner—Michael A. Brown
Attorney, Agent, or Firm—Yahwak & Associates

[57] ABSTRACT

A surgical drape apparatus that incorporates means to alleviate a patient's "suffocation anxiety" by providing for continued circulation of air to the patient's nose and mouth while the patient is draped for surgery, especially the field of surgery is the eye, is described.

12 Claims, 3 Drawing Sheets

SURGICAL APPARATUS

The present invention relates in general to the field of ophthalmic surgical drapes wherein the surgical field is the eye or the upper portion of the face wherein local anesthesia is used, and in particular to an apparatus for draping the head and/or body of a patient who is undergoing such surgery.

During surgery, especially ophthalmic surgery such as the removal of cataracts, plastic surgery, or the repair of retinal detachments, local anesthesia is used to provide the anesthesia required by the surgeon in order to successfully complete the surgical procedure. In addition to being awake during the procedure, the patient is covered with a surgical drape completely extending over the mouth, nostrils and face with just the surgical field exposed.

During surgery, some patients will move their heads to find a more comfortable position, and often as the surgery progresses the surgical drape, which initially rested lightly over the mouth and nose of the patient, tends to flatten itself snugly against the patient's nose and mouth for a number of reasons including the weight of the drape fabric and the weight of instruments placed upon the drape. The drape is impermeable to water and acts as an insulating barrier sequestering the patient's bodily heat and water vapor. This settling often results in an asphyxiation anxiety whereby the patient feels that the drape is suffocating even though the patient is actually receiving adequate amounts of oxygen by, for example, cannulae placed directly into the patient's nostrils. When such anxiety happens, the patient will often move their head in order to ease their perceived difficulty in breathing and to obtain an air space between the drape and the mouth and nostrils. Such movement is often unintentional by the patient and comes without warning to the surgeon. Any unexpected movement of the patient during a critical stage of the surgical procedure may be detrimental, especially in the case of ophthalmic surgeries, and thus such movement must be minimized. It is this desire to minimize risk to the patient that surgical drape supports are employed.

In addition to providing drape supports for surgical patients, patients are often provided with a means for maintaining a flow of air to the patient's face during surgery as either part of the drape support, or a separate device in addition to the support. Prior devices that have been developed to alleviate asphyxiation anxiety during surgery include those described in U.S. Pat. Nos. 3,403,677, 3,859,993, 4,122,848, 4,223,669, 4,699,131, and 5,140,997.

In U.S. Pat. No. 3,403,677 there is shown a "combined fluid supply apparatus and surgical drape support". This apparatus is a tubing that is connected at one end to a source of air or oxygen, and wherein the opposite end encircles the mouth and nose of the patient. A flow of air or oxygen is provided the patient by means of openings located at the mouth and nose-end of the tubing, and the outer diameter of the tubing provides a means for maintaining the surgical drape away from the patient's mouth and nose.

In U.S. Pat. No. 3,859,993, there is shown an "operating table accessory" which combines an instrument tray with an underlying ventilation fitting capable of delivering air to the underside of the surgical drape, or alternatively providing a suction to the underside of the drape at the surgeon's discretion.

In U.S. Pat. No. 4,122,848, there is shown "surgical drape support" that takes the form of a nose bridge-support being adhesively applied to the bridge of the patient's nose. The support has a "holder" extension leading away from the patient's face, and when placed over this holder, the surgical drape will remain away from the patient's nose and face. In addition, the support may have an optional clip attached to the holder for holding a hose for providing oxygen and/or air in proximity to the breathing area of the patient.

In U.S. Pat. No. 4,223,669, there is shown a "surgical drape support apparatus" that comprises a series of perforated tubes adapted to extend from under the neck to the top of the head, and from the mattress to above the head of the patient. In addition to maintaining the drape above the patient's head during surgery, an air or vacuum source may be attached to the support for providing air or a vacuum under the supported drape.

In U.S. Pat. No. 4,699,131, there is shown an "ophthalmic surgical drape support" that is generally in the shape of a air mask that creates a small tent about the nose and mouth of the patient into which oxygen may be supplied. This support is adapted to fit about the face of the patient and not to be attached to the patient's body.

In U.S. Pat. No. 5,140,997, there is shown an "ophthalmological surgical drape with breathing means" wherein the drape per se contains a permanently attached tube meant to be placed under the patient's nose and around the patient's mouth when the patient is covered with the drape. This support allegedly alleviates the need for any drape support since air or oxygen is to be provided directly to the nose and mouth of the patient during the surgery.

Even with these advances, however, there is still a need to develop a suitable surgical drape apparatus which will provide an optimum means for maintaining a surgical drape in the proper position for surgery on the eyes and upper head, and which will aid the patient in not having asphyxiation anxiety during those surgeries to the eyes and upper head portions.

Accordingly, it is one aspect of the present invention to describe a surgical drape apparatus for maintaining a surgical drape at a distance from the nostrils and mouth of a patient undergoing surgery.

It is another aspect of the present invention to describe a surgical drape apparatus for providing a flow of air and/or oxygen, preferably filtered oxygen and/or air, to the general area of the mouth and nostrils of a patient who is covered by a surgical drape that extends over the patient's mouth and nose.

It is another aspect of the present invention to describe a surgical drape apparatus for easy attachment to and removal from a patient prior to and subsequent to a surgical procedure;

It is still another aspect of the present invention to describe a surgical drape apparatus that substantially reduces or eliminates a patient's asphyxiation anxiety when undergoing a surgical procedure.

It is still another aspect of the present invention to describe a surgical drape apparatus that is disposable after each use.

A more thorough and better understanding of these and other aspects of the present invention may be had by reference to the following description and accompanying drawings in which.

Figure 1:
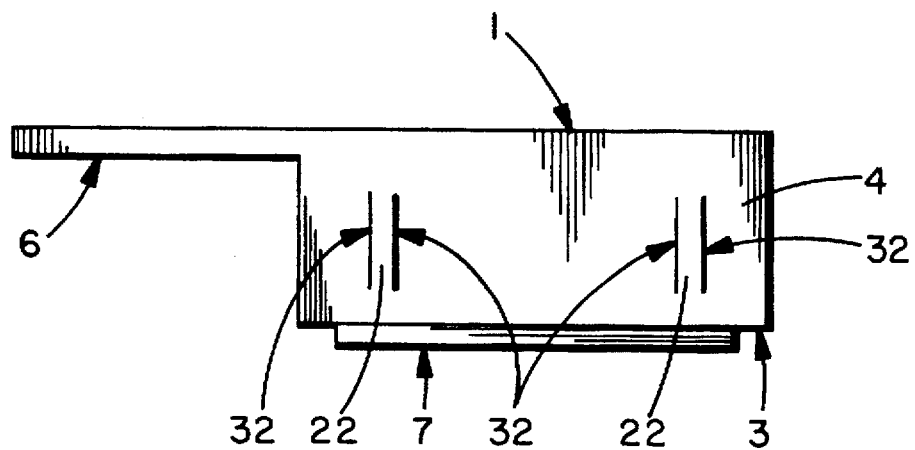
FIG. 1 is a side plan view of a surgical drape apparatus according to the present invention.
Figure 2:
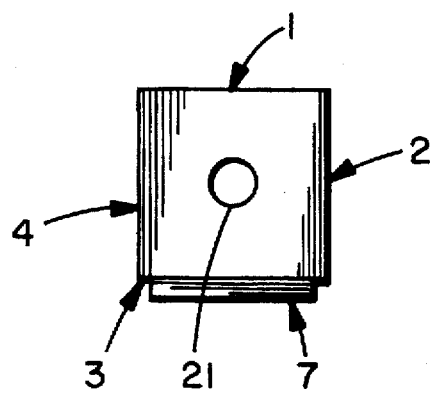
FIG. 2 is a rear plan view of a surgical drape apparatus according to the present invention.
Figure 3:
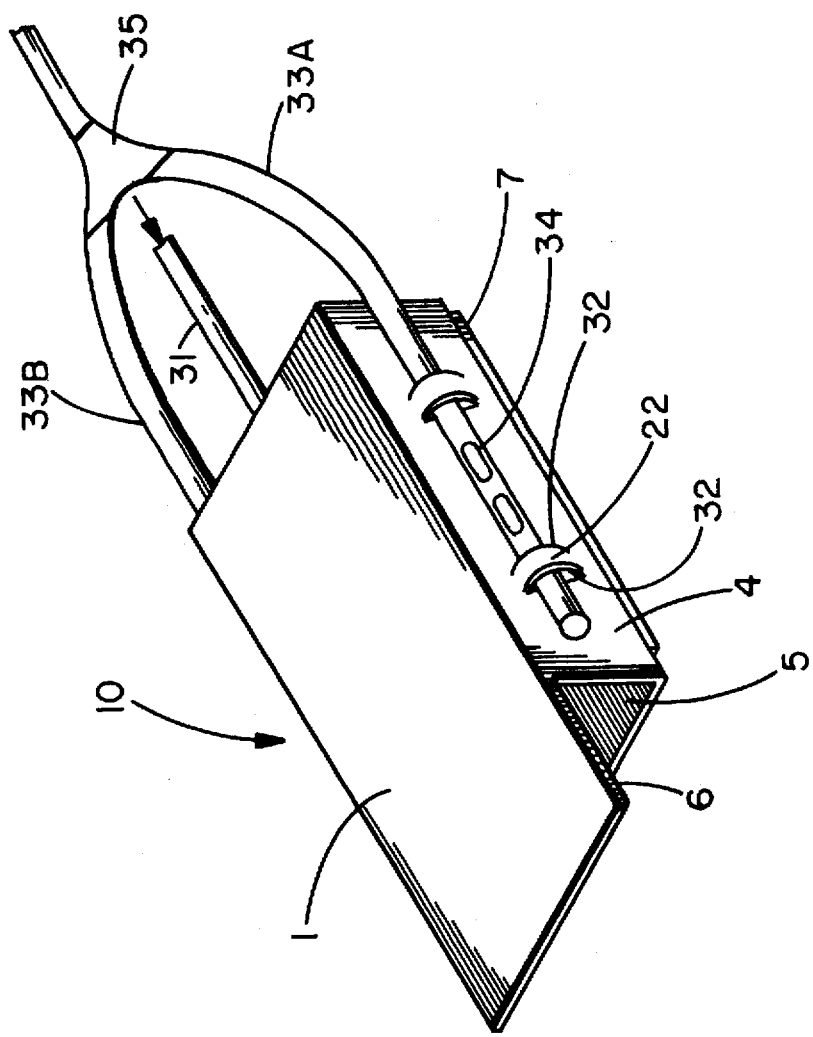
FIG. 3 is a three-quarters top plan view of a surgical drape apparatus according to the present invention.
Figure 4:
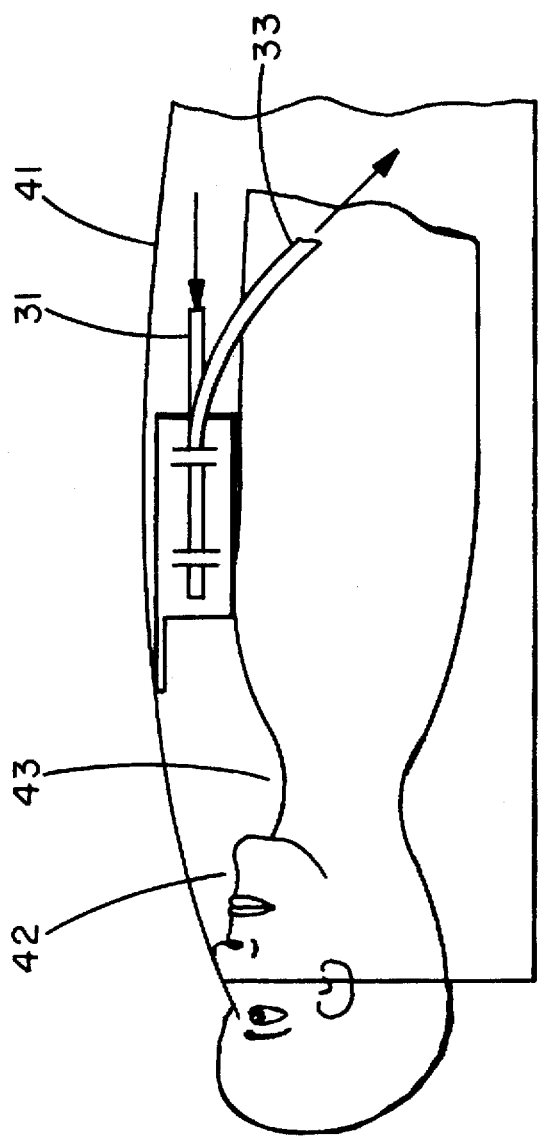
FIG. 4 is a side view of the surgical drape apparatus according to the present invention in place on a patient during surgery.

As depicted in the figures, there is shown a surgical drape apparatus according to the present invention which comprises a generally open-ended box 10 having a generally rectangular upper surface 1, a generally rectangular rear surface 2, a generally rectangular lower surface 3, and a pair of generally rectangular opposed side panels 4. The front of the apparatus is open thereby forming a front opening 5. As best seen in FIGS. 1, 2 and 3, the upper surface 1 extends forward of the side panels 4 to form an overhang 6 extending away from the apparatus 10 forward of the front opening 5. Although the dimensions of the apparatus according to the present invention may vary over a wide range depending upon whether it is manufactured for patients of different ages and sizes, or whether it is manufactured as a single-sized apparatus, it has been found that side panels measuring about 4–6 inches in length and 2–3 inches in width, and an upper surface measuring about 7–9 inches in length and 5–6 inches in width are adequate for most adult patients. Furthermore, although the apparatus may be manufactured from a wide range of materials which may be pre-sterilized for use in the operating room, it is preferred that the apparatus be manufactured from material such as paper or polymer stock that would allow for the apparatus to be easily and safely disposed of after each use.

The rear of the box contains an opening 21, preferably centrally located, that is adapted to hold an air tube or line 31 extending rearwardly away from the apparatus. The exterior surfaces of the side panels 4 of the apparatus contain at least one means 22 to hold an additional tube 33a or 33b along the panel 4 and extending rearwardly away from the panel. For ease of manufacture, this means may be a ring-tag formed by cutting a set of parallel slits 32 across a portion of the width of side panel 4 that will allow tubes (or lines) 33a–b to be inserted under the ring-tag and held in place along the length of the side panel. If necessary, additional ring-tags may be manufactured along side panels 4 for additional support of tubes 33a–b. In addition, the ring-tag may be replaced with other means for locking and holding tubes 33a–b in place, for example a separate tab having an opening for passing lines 33a–b therethrough may be manufactured and adhered to the side panels.

In use, a tube 31 will be inserted into opening 21 in such a manner that the tube 31 will be locked into the opening. If desired, tube 31 may be held within opening 21 by a locking means such as an O-ring, split-ring, or bushing. The opposite end of the tube will then be connected to a source of air or oxygen in such a manner as to deliver a flow of air or oxygen through tube 31 and into the rear of the apparatus 10.

While the ends of tubes 33a–b are open at its cross-section, additional perforations 34 may be made at the surface of the forward end of the tubes. As best shown in FIG. 3, tube 33a will be inserted under the means (ring-tag) 22 in one side panel 4, while tube 33b will be inserted under a similar means in the second side panel. The tubes will then be brought to the rear of the apparatus 10 and connected through a Y-connector 35 to a vacuum source (not depicted).

In use during a surgical procedure, the apparatus is set-up as shown in FIG. 3, placed on the upper chest of the patient undergoing by means of an adhesive pad 7 attached to the lower surface 3 of the apparatus, by tape, or by bandaging the apparatus to the patient; the manner in which the apparatus is held in place on the patient is not critical to the present invention. In addition to the adhesive pad 7 placed on the lower surface, and additional adhesive pad such a double-sided adhesive tape (not shown) may be placed on the upper surface of the apparatus; this will function to keep the surgical drape in place. In addition, if a similar piece of double-sided adhesive tape is placed on the bridge of the nose, the drape may be attached to the bridge of the nose as well, this "double suspension" will suspend the surgical drape above both the nose and mouth and help in preventing the drape from sagging in the middle. The overhang 6 is adjusted to be directed to the mouth and nasal area 42 of the patient's head, and all but the surgical field is covered by a surgical drape 41. An oxygen or air source (not depicted) is then activated in order to provide a flow of air or oxygen through tube 31 into the interior of the apparatus 10, thus providing a "flowing air" sensation into the ventilation space or air-pocket 43 formed by the upper surface 1, including its overlap 6, of the apparatus maintaining the drape 41 away from and above the mouth and nasal area 42 of the patient. A vacuum source is also activated in order to maintain withdraw the air and/or oxygen being fed into air-pocket 43 through lines 33a–b and to aid in maintaining the air flow circulation under the drape 41 by removing the stale and exhaled air within the air-pocket 43 and by providing for a flow of the air and/or oxygen being introduced into the air-pocket by line 31 away from the air-pocket. This results in an airflow which is both "inflow" through lines 31 and simultaneous "outflow" by vacuum lines 33 which in turn increases the air circulation for the patient.

The sensation of flowing air over the patient's lower face, and by providing a means to maintain the surgical drape above the mouth and nasal passages of the patient by both the apparatus according to the present invention and a "bubble" of flowing air and/or oxygen within the air pocket, is sufficient to alleviate the patient's asphyxiation anxiety. While others have provided for either a flow of oxygen or air under a surgical drape, or for the removal of stale air from under a surgical drape, the apparatus according to the present invention utilizes both vacuum and air lines to provide, in combination with a surgical drape support apparatus having means (the height of the apparatus and overlap 6) by which the surgical drape can be maintained above the mouth and nostrils of the patient, and by which a flow of air and/or oxygen may pass over the lower face of the patient to alleviate a patient's asphyxiation anxiety.

Thus, while we have illustrated and described the preferred embodiment of our invention, it is to be understood that this invention is capable of variation and modification, and we therefore do not wish or intend to be limited to the precise terms set forth, but desire and intend to avail ourselves of such changes and modifications which may be made for adapting the present invention to various usage's and conditions. Accordingly, such changes and modifications are properly intended to be within the full range of equivalents, and therefore within the purview of the following claims. The terms and expressions which have been employed in the foregoing specification are used as terms of description and not of limitation, and thus there is no intention, in the use of such terms and expressions, of excluding equivalents of the features shown and described, or portions thereof; the scope of the invention being defined and limited only by the claims which follow.

Having thus described our invention and the manner and process of making and using it in such full, clear, concise, and exact terms so as to enable any person skilled in the art to which it pertains, or with which it is most nearly connected, to make and use the same.

We claim:

1. A surgical apparatus for providing air circulation about the nose and mouth of a surgical patient, said apparatus being a generally rectangular box open at its forward end, said box having a rear panel, a pair of side panels, a bottom panel adapted to be placed on the chest of the patient and comprising a means for adhering the apparatus to the upper chest of a patient, and an upper panel extending forwardly beyond the side panels of said box and above and beyond the forward open end of said box.

2. A surgical apparatus according to claim 1 wherein the side panels comprise means for holding and supporting a hose or tube.

3. A surgical apparatus according to claim 1 wherein the rear panel has an opening passing therethrough, wherein the side panels contain means for holding a tube or hose in place along the exterior surfaces of each side panel.

4. A surgical apparatus according to claim 3 wherein the apparatus further comprises a tube extending through and rearwardly from said rear panel opening, and a tube extending along and rearwardly away from each side panel and held in place by said means for holding a tube or hose in place.

5. A surgical apparatus according to claim 4 wherein the tube extending through an opening in the rear panel is connected to a air and/or oxygen source.

6. A surgical apparatus according to claim 1 wherein the rear panel of the apparatus contains an opening for passage of an air line therethrough.

7. A surgical apparatus according to claim 6 wherein said air line is secured in said opening by a locking means.

8. A surgical apparatus according to claim 1 which further comprises a means on each of said side panels for attachment and securing of an air line to the exterior of said apparatus.

9. A surgical apparatus according to claim 8 wherein the means is a ring-tab.

10. A surgical apparatus according to claim 8 wherein air lines extending along and rearwardly away from each side panel are co-joined to a Y-connector and said connector is joined to a vacuum source.

11. A method to alleviate suffocation anxiety in a surgical patient that comprises;

providing an apparatus for circulating air about the nose and mouth of a surgical patient, said apparatus having means extending from said apparatus for maintaining a surgical drape above the neck of a patient;

attaching the apparatus to the chest of a patient with said means extending over the patient's neck;

draping the patient with a surgical drape extending from the nose of the patient over the apparatus and to a point below the site on the patient's chest where the apparatus is attached, said drape and said means forming an air space between the drape and the neck of the patient and from the apparatus to the nose of the patient; and providing air circulation within said air space by causing air to enter the air inlet line of said apparatus, and by removing air from said air space through said exhaust air line.

12. A method according to claim 11 which further comprises said apparatus being a generally rectangular box open at its forward end, said box having a rear panel containing a opening and having an inlet air line extending therethrough, a pair of side panels each panel having an exhaust air line attached thereto, a bottom panel adapted to be placed on the chest of the patient, and an upper panel extending forwardly beyond the side panels of said box and above and beyond the forward open end of said apparatus.

* * * * *